United States Patent [19]

Shay et al.

[11] Patent Number: 5,071,762

[45] Date of Patent: Dec. 10, 1991

[54] ENHANCING THE FLAVOR OF PROTEIN PRODUCTS DERIVED FROM MICROORGANISMS

[75] Inventors: Lucas K. Shay, Bartlesville; Trudy J. Fisher, Catoosa, both of Okla.

[73] Assignee: Phillips Petroleum Company, Bartlesville, Okla.

[21] Appl. No.: 566,723

[22] Filed: Aug. 13, 1990

[51] Int. Cl.$^5$ .................... C12N 1/32; C12N 1/00; C12P 7/40; A23L 1/28
[52] U.S. Cl. .................................. 435/247; 435/136; 435/921; 426/60; 426/62
[58] Field of Search ............... 435/247, 136, 921; 426/60, 62

[56] References Cited

U.S. PATENT DOCUMENTS

| | | |
|---|---|---|
| 3,865,691 | 2/1975 | Ridgway et al. ............ 435/247 |
| 3,868,305 | 2/1975 | Masuda et al. ............. 435/247 |
| 3,879,261 | 4/1975 | Matsumoto et al. ......... 435/247 |
| 3,981,774 | 9/1976 | Hitzman ................... 435/247 |
| 4,326,032 | 4/1982 | Grove ..................... 435/148 |
| 4,520,102 | 5/1985 | Bunno et al. .............. 435/61 |
| 4,567,144 | 1/1986 | Neidleman et al. .......... 435/134 |
| 4,617,274 | 10/1986 | Wegner .................... 435/255 |

OTHER PUBLICATIONS

*Biology*, 2nd edition (R. A. Goldsby, 1979, Harper and Row, New York), pp. 135-137.
*Biochemistry* (A. L. Lehniger, 1970, Worth Publishers, New York), pp. 426-427.
A. E. Humphrey, "Production of Single Cell Protein from Ethanol", Advances in Biotechnology 2: pp. 431-437, (1981), Humphrey.
C. T. Hou, et al., "Substrate Specificity and Stereospecificity of Nicotinamide Adenine Dinucleotide-Linked Alcohol Dehydrogenases from Methanol-Grown Yeasts", App. and Envir. Micro. 41, pp. 829-832 (1981).

*Primary Examiner*—Douglas W. Robinson
*Assistant Examiner*—Michael Meller
*Attorney, Agent, or Firm*—Hal Brent Woodrow

[57] ABSTRACT

The present invention provides a process for the enhancement of the flavor of proteins derived from dried microorganisms comprising a) contacting a fermentation broth contining a suitable viable microorganism culture with a suitable sugar under suitable anerobic conditions for the cultivation of said microorganism from about 20 minutes to about 10 hours;

b) cultivating the fermentation broth under suitable conditions to facilitate the conversion of the suitable sugar contacted therewith to an alcohol, thereby forming a fermentation mixture; followed by c) aerobically cultivating said fermentation mixture;

d) contacting said fermentation mixture with a suitable quality of one or more suitable short chain alcohols to form a fermentation admixture;

e) cultivating said fermentation admixture under suitable conditions to facilitate the conversion of said one or more short chain alcohols to the corresponding carboxylic acids thereby forming a fermentation effluent; and f) drying said fermentation effluent to recover an improved dried microorganism product.

6 Claims, No Drawings

ENHANCING THE FLAVOR OF PROTEIN PRODUCTS DERIVED FROM MICROORGANISMS

FIELD OF INVENTION

The present invention pertains to a process for enhancing the flavor of protein products which are derived from microorganisms. Another aspect of the invention pertains to protein products derived from microorganisms which have an enhanced flavor.

BACKGROUND OF THE INVENTION

As a result of the current worldwide shortage of foods possessing a high protein content, there has been a great deal of research directed toward producing proteins from microorganisms. This research has led to the successful production of high quality protein products from microorganisms.

However, these protein products have not gained a widespread commercial acceptance. One of the primary reasons for this lack of commercial acceptance, is that these proteins often have a rather bland flavor that is unacceptable to most consumers. Attempts have been made to solve this problem, but none of the solutions currently available have been entirely successful.

Therefore, it would be a valuable contribution to the art to develop a process that would enhance the flavor of protein products that are derived from microorganisms.

It is an object of the present invention to provide a process that will enhance the flavor of protein products derived from microorganisms.

Other aspects, objects, and several advantages of this invention will be apparent from the foregoing specification examples and claims.

SUMMARY OF THE INVENTION

In accordance with the present invention we have discovered a process that will enhance the flavor of protein products derived from dried microorganisms comprising:
a) contacting a fermentation broth containing a suitable viable microorganism culture for the production of food with at least one suitable sugar wherein said sugar can be metabolized during anaerobic fermentation by said microorganism culture to an alcohol; thereafter
b) anaerobically cultivating said microorganism while in contact with said at least one suitable sugar under suitable conditions for an effective amount of time, to facilitate the conversion of a substantial portion of the at least one suitable sugar to an alcohol thereby forming a fermentation mixture; thereafter
c) contacting said fermentation mixture with a suitable quantity of at least one suitable short chain alcohol to form a fermentation admixture; thereafter
d) cultivating said fermentation admixture under suitable conditions to facilitate the conversion of said at least one suitable short chain alcohol to the corresponding carboxylic acid thereby forming a fermentation effluent; and
f) drying said fermentation effluent under suitable conditions to retain a substantial portion of said corresponding carboxylic acid to recover an improved dried microorganism product.

DETAILED DESCRIPTION OF THE INVENTION

The present invention provides a process for improving the flavor of protein products produced by microorganisms. An improved flavor for microbially produced proteins can be produced by converting suitable short chain alcohols to the corresponding carboxylic acids during fermentation. Suitable short chain alcohols for the practice of this invention are defined as short chain alcohols selected from the group consisting of n-propanol, n-butanol, n-hexanol and combinations of two or more thereof. Normally yeasts and bacteria which are utilized in the production of food products do not metabolize short chain alcohols to the corresponding carboxylic acids, during aerobic fermentation. However, we have discovered that by shifting from anaerobic growth conditions to aerobic conditions that the microorganism involved in the fermentation which produced an alcohol dehydrogenase or like enzyme during the anaerobic fermentation in response to the presence of a suitable sugar, will convert short chain alcohols to the corresponding carboxylic acids during a subsequent aerobic fermentation. By selecting the appropriate short chain alcohols or mixtures thereof, which will be converted into carboxylic acids, the flavor of the fermentation broth can be improved.

The process of the present invention can be utilized with facultative anaerobes capable of producing nontoxic proteins suitable for use in human and animal food products. Suitable microorganisms for the practice of the present invention include bacteria and yeasts. Yeasts are presently preferred for the practice of this invention. Suitable yeasts include species from the genera Candida, Kluyveromyces, Hansenula, Saccharomyces, and Pichia. Examples of suitable species of yeast include yeast selected from the group consisting of: *Candida boidinii, Hansenula saturnus, Candida utilis, Hansenula californica, Candida stellatoidea, Hansenula mrakii, Candida robusta, Hansenula silvicola, Candida sake, Hansenula polymorpha, Candida claussenii, Hansenula wickerhamii, Candida rugosa, Hansenula capsulata, Hansenula minuta, Hansenula glucozyma, Hansenula nonfermentans, Hansenula henricii, Pichia farinosa, Pichia membranefaciens, Pichia polymorpha, Pichia pinus, Kluyveromyces lactis, Pichia pastoris, Pichia trehalophila, Saccharomyces cerevisiae, Kluyveromyces fragilis, Saccharomyces rosei, Saccharomyces bailii, Saccharomyces uvarum,* and *Saccharomyces elegans, Saccharomyces rouxii.*

Suitable bacteria include species from the generus Zymomonas. An example of suitable species of bacteria is: *Zymomonas mobilis.*

The most preferred microorganisms for use in the present invention include those yeasts which are currently approved by the FDA for human consumption. Examples of suitable species include *Candida utilis, Saccharomyces cerevisiae, Kluyveromyces fragilis,* and *Saccharomyces uvarum.*

Typically microorganisms are initially cultured by growing them on a suitable carbon energy source, under aerobic aqueous fermentation conditions employing an assimilable nitrogen source, mineral salts, molecular oxygen, with suitable pH and other controls, as are known in the art.

The particular fermentation method and apparatus used to culture the chosen microorganism is not critical to the practice of the present invention. There are numerous fermentation processes and apparatuses that are well known to those skilled in the art. Any of these well known fermentation processes and apparatuses are suitable for use with the present invention, provided it is appropriate for that particular microorganism. For example, U.S. Pat. No. 4,617,274, Biochemical Conversions by Yeast Fermentation at High Cell Densities, issued to Eugene Wegner, which is currently assigned to Phillips Petroleum Company, teaches a suitable fermentation technique for use in the present invention.

After a suitable cell density is achieved the fermentation broth should be contacted with at least one sugar suitable for the microorganism to utilize anaerobically as a carbon-energy source to yield an alcohol such as ethanol. For example, at least one suitable sugar for the yeast *Candida utilis* is a sugar selected from the group consisting of glucose, fructose, sucrose, mannose, sorbitol, and maltose. Those skilled in the art will be readily able to determine suitable sugar sources for the microorganisms of the present invention.

The purpose of the anaerobic fermentation of the microorganism is to induce the production of alcohol dehydrogenase or like enzymes which are not present during aerobic fermentation. When the fermentation is returned to aerobic fermentation conditions, the presence of the alcohol dehydrogenase will enable the microorganism to convert short chain alcohols present to the corresponding carboxylic acid.

The microorganisms should be maintained under anaerobic conditions until a substantial amount of the at least one suitable sugar is converted by the microorganisms to an alcohol. However, anaerobic fermentation should be discontinued before the concentration of alcohol in the fermentation broth reaches a level toxic to the microorganism being cultivated. The amount of at least one suitable sugar should range from about 5 gram/liter to about 300 gram/liter based on the weight of the fermentation broth.

The anaerobic fermentation conditions should also employ an assimilable nitrogen source and mineral salts at a suitable pH to maintain the viability of the microorganisms in the fermentation broth. The apparatus and fermentation conditions necessary to carry out anaerobic fermentation are well known to those skilled in the art. Anaerobic fermentation should be conducted for a sufficient amount of time to result in the formation of alcohol from the at least one sugar empolyed. Generally, the time required is in the range of from about 20 minutes to about 10 hours, depending on the fermentaion conditions, microorganism, and amount and type of sugar or sugars employed.

Aerobic fermentation should be reinitiated after a substantial amount of the at least one sugar has been converted to alcohol or before the alcohol concentration in the fermentation broth reaches levels toxic to the microorganism being cultivated. The short chain alcohol may be added to or contacted with the fermentation broth, before reinitiation of aerobic fermentation, contemporaneous with the reinitiation of aerobic fermentation, or after the alcohol produced during the aerobic fermentation is consumed. Suitable short chain alcohols for the practice of this invention are defined as short chain alcohols selected from the group consisting of n-propanol, n-butanol, n-hexanol and combinations of two or more thereof. The amount of short chain alcohol contacted with the fermentation broth should be an effective amount to impart a flavor to the fermentation broth after it is converted by the microorganism to the corresponding carboxylic acid (propanoic acid, butyric acid and caproic acid), while not being provided in amounts toxic or inhibitory to the microorganism being cultivated in the fermentation broth. By way of guidance for the yeast *Candida utilis* it is recommended that the amount of at least one suitable short chain alcohol range from about 1 g/l to about 100 g/l depending on the desired intensity of flavor in the final product. The aerobic fermentation should be conducted in a manner which facilitates the conversion of a substantial portion of the at least one short chain alcohol to its corresponding carboxylic acid. For cultivating the microorganism at this stage of the fermentation the microorganism should be grown under carbon limited conditions to facilitate the conversion of the short chain alcohol to the corresponding carboxylic acid.

Once the desired degree of conversion has been achieved the fermentation broth may be heat treated to terminate the fermentation (by heating to 80° C.) or any other technique conventionally used which does not entail a step that would remove soluble ingredients. The fermentation effluent may then be spray dried or further treated to facilitate shipping and handling.

Examples are provided to assist in a further understanding of the invention. Particular materials employed, species, and conditions are intended to be further illustrative of the invention and not a limitation thereof.

EXAMPLE 1

The purpose of this example is to demonstrate that the flavor of the protein products produced in accordance with the prior art is unappealing to most consumers.

In a continuous aerobic fermentation process, aqueous mineral salts medium and sucrose were fed to a fermentor inoculated with the yeast species Candida utilis NRRL Y-1082, at a rate such that sucrose was the growth-limiting nutrient. The fermentor was a 4-liter foam-filled fermentor with a liquid volume of about 1.5 liters, with automatic pH, temperature, and level control. Agitation was provided by two conventional paddle-type turbines driven at 800 rpm. The aeration rate was about 4 volumes of air per volume of ferment in the fermentor per minute. Anhydrous ammonia was added at a rate sufficient to maintain a pH of about 4 in the fermentation mixture.

The aqueous fermentation medium was prepared by mixing, with each liter of tap water, 11.9 mL of 75 weight percent $H_3PO_4$, 6.4 g of $K_2SO_4$, 5 g of $MgSO_4.7H_2O$, 0.3 g of $CaSO_4.2H_2O$, 1.8 g of 85 weight percent KOH, and 275 g of sucrose. The aqueous fermentation medium was fed into the fermentor at a rate of 250 to 300 mL per hour.

The trace mineral solution was prepared by mixing for each liter of solution 60 g of $FeSO_4.7H_2O$, 1.5 g of $Na_2MoO_4.2H_2O$, 0.2 g of $CoCl_2.6H_2O$, 38 g of $ZnSO_4.7H_2O$, 2.5 g of $MnSO_4.H_2O$, 5 g of $CuSO_4.5H_2O$ and 4 mL of concentrated $H_2SO_4$ and sufficient deionized water to make 1 liter of solution. The trace mineral solution was fed into the fermentor at a rate of 1.0 to 1.2 mL per hour.

The fermentation was conducted at about 34° C. with an average retention time of about 5 to 6 hours. The cell density was typically about 140 grams of cells per liter of fermentor broth. The total solid contents of the fermentor was typically about 150 grams per liter.

The resulting yeast cells were separated from the fermentation broth by centrifugation, washed by suspension in water, followed by recentrifugation, dried via a spray drier and weighed. On a dried basis the yield of yeast cells typically was about 50 to 54 g per 100 g of sucrose.

Yeast produced in this manner had a very bland flavor that was found unappealing by the taste tester. They had an off-white color.

EXAMPLE II

This example illustrates how yeast cells grown in a fermentor are physiologically manipulated for the production of desirable flavor(s).

The air/oxygen supply to a continuous culture as described in Example I was terminated and was simultaneously replaced with $N_2$. In the meantime, the fermentor was supplied with an additional 100 mL of fresh feed containing 27.5 g sucrose and 0.4 mL trace mineral solution as described in the previous example. The culture was maintained anaerobically for 5.5 hours. During this period, alcohol was formed and was monitored by a GC and dissolved oxygen response. After the fermentation was shifted to aerobic fermentation the alcohol formed during the anaerobic fermentation was consumed.

This physiologically or environmentally manipulated yeast culture was then used to convert short chain alcohols, such as propanol, butanol, hexanol, to their corresponding fatty acids, propionic acid, butyric acid, and caproic acid.

These short chain alcohols were added slowly such that the alcohols were converted to their corresponding acids instantly. This was done by monitoring the dissolved oxygen response.

For instance, 7.0 mL of propanol and 10.0 mL of butanol were slowly and continuously added to the manipulated culture during a 16 min. span. The resulting culture was then harvested for the determination of fatty acid content and flavor.

An aliquot, 100 mL of the culture, was placed in a round bottom flask for steam distillation to recover the fatty acids and to discard the aqueous suspension containing yeast cells and spent medium. The steam-distilled sample was filtered through an on-line membrane filter (0.45 μm) followed by injection into a stainless steel gas chromatographic column (6'×⅛") equipped with Supelco's GP10%sp-1200/1% $H_3PO_4$ on 80/100 chromasorb WAW in an HP 5712A gas chromatograph. The oven temperature was programmed at 90° C. for 8 min. and 16° C./min with a final temperature of 180° C. for 16 min. A mixture of authentic samples containing $C_2$–$C_{10}$ fatty acids were used as standard.

The results showed that the distilled sample contained 0.56% butyric acid corresponding to 89% conversion, and 0.43% propionic acid, corresponding to 98% conversion.

The rest of the culture was heated to 80° C. followed by spray drying at an inlet temperature of 130° C. and an outlet temperature of 95° C. The spray-dried product had a very buttery taste.

This example also demonstrates that, though the yeast has enzymatic systems to assimilate ethanol for the biosynthesis of cellular materials, it lacks enzymatic systems to use higher alcohols as substrates for growth.

EXAMPLE III

This example illustrates that non-manipulated yeast culture is incapable of converting higher alcohol to its corresponding acid.

The experiment was carried out as in Example II except that the culture employed was not physiologically manipulated, i.e., the culture used was the culture described in Example I, and butanol was the only alcohol used. The results showed that there was little or no dissolved oxygen response upon butanol addition and the recovered sample contained almost all butanol that was added. This experiment clearly demonstrates that, in order to produce yeast having flavor short chain fatty acids, characteristics of some cheddar cheese flavor, the yeast culture must have been manipulated as described in Example II.

That which is claimed is:

1. A process for providing an edible buttery or cheese flavor to a dried microorganism product comprising
    a) contacting a fermentation broth containing a suitable viable microorganism culture for the production of food; wherein the microorganism is selected from the group consisting of: *Candida boidinii, Hansenula saturnus, Candida utilis, Hansenula californica, Candida stellatoidea, Hansenula mrakii, Candida robusta, Hansenula silvicola, Candida sake, Hansenula polymorpha, Candida claussenii, Hansenula wickerhamii, Candida rugosa, Hansenula capsulata, Hansenula minuta, Hansenula glucozyma, Hansenula nonfermentans, Hansenula henricii, Pichia farinosa, Pichia membranefaciens, Pichia polymorpha, Pichia pinus, Kluyveromyces lactis, Pichia pastoris, Pichia trehalophila, Saccharomyces cerevisiae, Kluyveromyces fragilis, Saccharomyces rosei, Saccharomyces bailii, Saccharomyces rouxii* and *Zymomonas mobilis* with at least one suitable sugar wherein said sugar can be metabolized during anaerobic fermentation by said microorganism culture to an alcohol; thereafter
    b) anaerobically cultivating said microorganism while in contact with said at least one suitable sugar under suitable conditions for an effective amount of time, to facilitate the conversion of a substantial portion of the at least one suitable sugar to an alcohol thereby forming a fermentation mixture; thereafter
    c) contacting said fermentation mixture with a suitable quantity of at least one suitable short chain alcohol to impart a buttery or cheese flavor when converted to the corresponding carboxylic acid, wherein the short chain alcohol is selected from the group consisting of n-propanol, n-butanol, and n-hexanol to form a fermentation admixture; thereafter
    d) cultivating said fermentation admixture aerobically under suitable conditions to facilitate the conversion of said at least one suitable short chain alcohol to the corresponding carboxylic acid thereby forming a fermentation effluent; and
    f) drying said fermentation effluent under suitable conditions to retain a substantial portion of said corresponding carboxylic acid to recover an edible dried microorganism, with a buttery or cheese flavor.

2. The process of claim 1 wherein the microorganism culture is selected from the group consisting of *Candida utilis, Saccharomyces cerevisiae, Kluyveromyces fragilis*, and *Saccharomyces uvarium*.

3. The process of claim 1 wherein the microorganism culture is a culture of *Candida utilis*.

4. The process of claim 3 wherein the suitable sugar is selected from the group consisting of glucose, fructose, sucrose, mannose, sorbitol and maltose.

5. The process of claim 1 wherein the amount of at least one suitable sugar is in the range of from about 5 gram/liter to about 300 gram/liter.

6. The process of claim 3 wherein the amount of at least one suitable short chain alcohol is in the range of from about 1 gram/liter to about 100 grams/liter.

* * * * *